(12) United States Patent
Gauthier et al.

(10) Patent No.: US 8,087,308 B2
(45) Date of Patent: Jan. 3, 2012

(54) PROBE FOR REMOVAL OF PARTICULATES FROM GAS SAMPLING STREAM

(75) Inventors: Philippe Jean Gauthier, Fullerton, CA (US); Neil Colin Widmer, San Clemente, CA (US)

(73) Assignee: General Electric Company, Schenectady, NY (US)

( * ) Notice: Subject to any disclaimer, the term of this patent is extended or adjusted under 35 U.S.C. 154(b) by 439 days.

(21) Appl. No.: 12/368,351

(22) Filed: Feb. 10, 2009

(65) Prior Publication Data

US 2010/0199787 A1 Aug. 12, 2010

(51) Int. Cl.
*G01N 1/22* (2006.01)
(52) U.S. Cl. .................. 73/863.23; 73/863.41
(58) Field of Classification Search .......... 73/863.23, 73/863.41, 863.51, 863.57
See application file for complete search history.

(56) References Cited

U.S. PATENT DOCUMENTS

| | | | |
|---|---|---|---|
| 3,961,896 A * | 6/1976 | Dunn | 436/173 |
| 4,161,883 A | 7/1979 | Laird et al. | |
| 4,286,472 A * | 9/1981 | Pocock | 73/863.24 |
| 4,653,334 A * | 3/1987 | Capone | 73/863.81 |
| 4,856,352 A | 8/1989 | Daum et al. | |
| 5,824,919 A * | 10/1998 | Hansen | 73/863.23 |
| 6,869,800 B2 * | 3/2005 | Torgerson et al. | 436/37 |
| 7,337,683 B2 | 3/2008 | DeFriez et al. | |
| 7,523,680 B2 * | 4/2009 | Zimmer et al. | 73/863.23 |

FOREIGN PATENT DOCUMENTS

| | | | |
|---|---|---|---|
| EP | 244936 | * 11/1987 | 73/863.23 |
| GB | 1443465 | 7/1979 | |
| JP | 2000-227389 A | 8/2000 | |
| SU | 455263 | 12/1974 | |

OTHER PUBLICATIONS

EP 10152743.0 European Search Report, Jul. 14, 2010.
Abstract of Soviet Patent SU 455263, Apr. 24, 1975, 1 page.

* cited by examiner

*Primary Examiner* — Daniel Larkin
(74) *Attorney, Agent, or Firm* — Cantor Colburn LLP

(57) ABSTRACT

A sample probe includes a sample probe tip filter. The sample probe also includes a shield disposed in relation to the sample probe tip filter, the shield being operable to deflect particles in a gas sampling stream away from the sample probe tip filter. The shield has at least one opening that allows the gas within the gas sampling stream and certain ones of the particles in the gas sampling stream both traveling in a substantially flow reversal direction to a primary direction of the gas sampling stream to enter the shield and contact the sample probe tip filter.

19 Claims, 3 Drawing Sheets

US 8,087,308 B2

PROBE FOR REMOVAL OF PARTICULATES FROM GAS SAMPLING STREAM

BACKGROUND OF THE INVENTION

The subject matter disclosed herein relates to a gas stream sampling probe and, in particular, a probe for reducing the number of particulates from entering a sample probe at the sampling location of a gas stream.

Fly ash is one of several pollutant particulate residues generated in the combustion of coal or other fossil fuels by, e.g., boilers or furnaces. Fly ash is generally captured from the chimneys of coal-fired power plants. In the past, fly ash was generally released into the atmosphere, but recent mandates require pollution control equipment to capture the fly ash instead of releasing it into the environment. In the U.S., the fly ash is now generally collected and stored at the power plant. Depending upon the source and makeup of the coal being burned, the components of the fly ash produced vary considerably, but fly ash typically includes substantial amounts of silicon dioxide ($SiO_2$) (both amorphous and crystalline) and calcium oxide ($CaO$). Fly ash is commonly used to supplement cement in concrete production, where it can bring both technological and economic benefits, and is increasingly finding use in the synthesis of geopolymers and zeolites.

However, when sampling a gas stream, for example, in a combustion furnace or boiler operating at relatively high temperatures (e.g., 900° F.-1500° F.), it is generally difficult to continuously separate on-line or in-situ the relatively hot fly ash from the sampling flue gas such that primarily the flue gas is sensed. Removal of fly ash in a relatively substantial amount from the gas sampling stream at or near the sample probe or sensor is needed for typical sampling applications. Failure to reduce the amount of fly ash leads to: 1) ash accumulation within the sampling probe, which may lead to plugging of the probe; and 2) ash accumulation on the analyzer's sensors, which may reduce or impair the sensing ability and accuracy and also the lifetime of the sensors.

There exist many techniques to remove fly ash from hot flue gas sampling streams. A common technique is to use a sampling conditioning system to cool down the temperature of the sample flue gas. The separation of fly ash from the sample flue gas stream is then performed via a filtering device such as a fabric filter, cyclone, or other filtering device system. This approach turns out to be cumbersome and expensive due to the additional parts needed. In addition, this type of system usually requires relatively high maintenance due to ash disposal requirements from the filtering system.

BRIEF DESCRIPTION OF THE INVENTION

According to one aspect of the invention, a sample probe includes a sample probe tip filter. The sample probe also includes a shield disposed in relation to the sample probe tip filter, the shield being operable to deflect particles in a gas sampling stream away from the sample probe tip filter. The shield has at least one opening that allows the gas within the gas sampling stream and certain ones of the particles in the gas sampling stream both traveling in a substantially flow reversal direction to a primary direction of the gas sampling stream to enter the shield and contact the sample probe tip filter.

According to another aspect of the invention, A sample probe for sampling flue gas in a gas sampling stream includes a sample probe filter having a tip portion located at one end of the sample probe filter, the tip portion of the sample probe filter being operable to sample the flue gas in the gas sampling stream. The sample probe also includes a shield disposed in relation to the sample probe filter, the shield having a length that at least substantially covers the sample probe filter, the shield being operable to deflect particles in the gas sampling stream away from the sample probe tip filter. The shield has at least one opening that allows the gas within the gas sampling stream and certain ones of the particles in the gas sampling stream both traveling in a substantially flow reversal direction to a primary direction of the gas sampling stream to enter the shield through the at least one opening and contact the sample probe tip filter.

According to yet another aspect of the invention, a sample probe includes a sample probe tip filter and a shield disposed in relation to the sample probe tip filter such that the shield substantially covers the sample probe tip filter. The shield has an inner pipe and an outer pipe, the outer pipe having at least one opening that allows gas within a gas sampling stream and certain ones of particles in the gas sampling stream both traveling in a substantially flow reversal direction to a primary direction of the gas sampling stream to enter the shield and contact the sample probe tip filter.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings in which:

FIG. 2, including FIG. 3, including

The detailed description explains embodiments of the invention, together with advantages and features, by way of example with reference to the drawings.

DETAILED DESCRIPTION OF THE INVENTION

Figure 1:
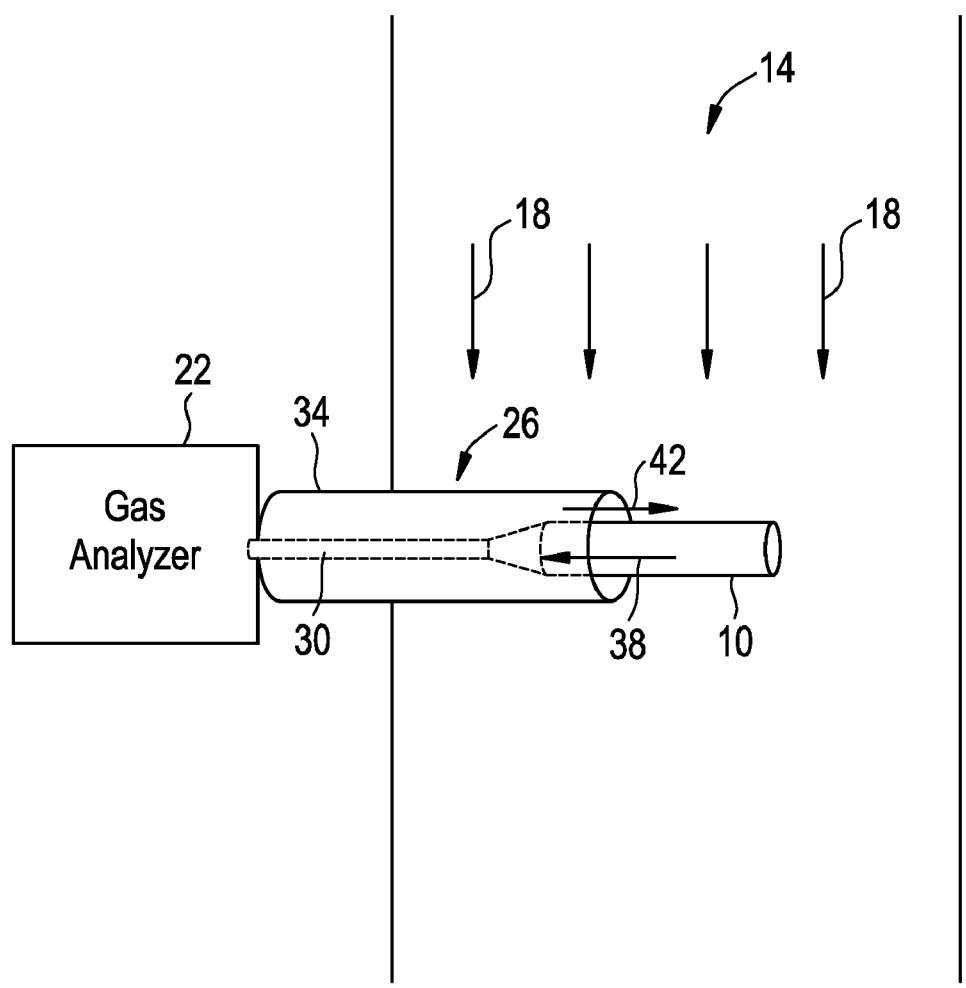
FIG. 1 illustrates an embodiment of a sample probe inserted in a flue gas stream.

In FIG. 1 is an embodiment of a sample probe filter 10 inserted in a relatively hot flue gas stream 14 within, e.g., a furnace or boiler. The high temperature flue gas (e.g., 900° F. to 1500° F.) may travel downward as indicated by the lines with arrowheads 18, where reference number 18 indicates a travelling gas stream. The traveling gas stream 18 contacts the sample probe filter 10 typically at a ninety-degree angle as shown, but may contact the filter 10 at other angles as well. Also, the flue gas may travel in any other direction, such as horizontally through a corresponding horizontally oriented flue gas path. The hot flue gas typically contains undesirable (e.g., pollutant) particulate matter such as fly ash. The flue gas enters the sample probe filter 10 due to a vacuum pressure created by a vacuum system associated with the gas analyzer equipment 22. The analyzer sample probe 26 also comprises at least one pipe section 30. The sample probe filter 10 is disposed within the pipe section 30 and a tip portion of the sample probe filter 10 is located at the end of the pipe section 30, with the pipe section 30 and probe tip filter 10 protruding into the flue gas stream 14. The pipe section 30 and probe tip filter 10 may be inserted within a support sleeve pipe 34, which supports the sample probe pipe section(s) 30. If more than one pipe section 30 is utilized, these sections 30 may be connected together to form one contiguous pipe section 30. The support sleeve pipe 34 is utilized to avoid bending of relatively long sample probes 26 (e.g., three to twenty feet) inside the furnace. The sample probe tip filter 10 may extend beyond the support sleeve pipe 34 by, e.g., a few inches to collect flue gas 14 from the combustion furnace. The flue gas 14 enters through the probe tip filter 10, flows through the sample probe pipe section(s) 30 as indicated by the line with the arrowhead 38 in FIG. 1, and through the sensors within the analyzer 22. The sampled flue gas is then released back into the hot combustion furnace gas stream 14 via a gas pathway indicated by the line with the arrowhead 42 in FIG. 1 and defined between the support sleeve pipe 34 and the sample probe pipe section(s) 30.

Figure 2A:
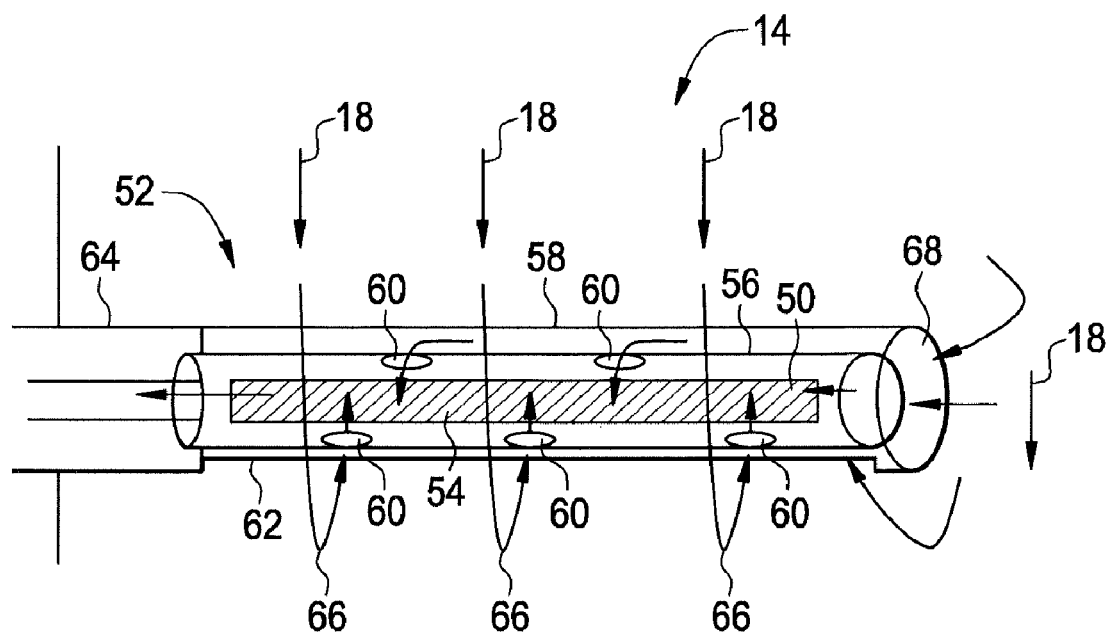
FIGS. 2A and 2B, are side and end views, respectively, that together illustrate a sample probe with a shield in accordance with an embodiment of the invention.
Figure 2B:
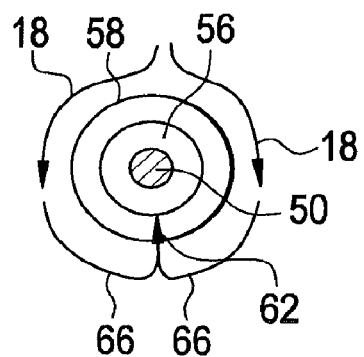

In FIG. 2, including FIGS. 2A and 2B taken together, a sample probe tip filter 50 includes a shield configuration 52, which reduces the amount of fly ash particulates within the travelling gas stream 18 that impinge on the probe tip filter 50, according to an embodiment of the invention. The shield 52 of FIG. 2 uses a flow reversal technique to reduce the amount of fly ash particulates in the travelling gas stream 18 that enter the sample probe tip filter 50. In an embodiment, the fabric filter portion 54 of the sample probe tip filter 50 is enclosed within two concentric pipes 56, 58. The pipes 56, 58 may be cylindrical or other suitable shapes, and may comprise steel or other suitable material. Also, there may be only one pipe, or more than two pipes in various embodiments. The inner concentric pipe 56 may have one or more openings 60 along its length that allows for the sampling flue gas to enter and contact the fabric filter portion 54. The openings 60 may comprise slots, perforations or other suitable opening configurations. In an embodiment, the outer concentric pipe 58 may have one or more openings 62 (e.g., a slot or other type of opening) located on the downstream side of the pipe 58 as viewed in FIGS. 2A and 2B, for example, a single opening 62 is located along the entire length of the downstream side of the outer concentric pipe 58 with respect to the inner concentric pipe 56. Other opening configurations for the outer pipe 58 are possible. Also in an embodiment, a support sleeve pipe 64 may be provided that connects with the inner and/or outer concentric pipes 56, 58 and with the analyzer 22 (FIG. 1).

The shield 52 of FIG. 2 uses the flow entrainment force and gravimetric force to reduce the amount of fly ash that enters the sample probe tip filter 50. As shown in FIGS. 2A and 2B, the travelling gas stream 18 flows downward within the furnace 14. The travelling gas stream 18 encounters the shield configuration 52, which diverts the flow of the travelling gas stream 18 around the shield 52. The travelling gas stream 18 then makes a 180 degree "U-turn", or directional flow reversal, as illustrated by the lines with arrowheads 66, and flows back through the openings 62, 60 in the outer and inner concentric pipes 58, 56, respectively. The travelling gas stream 18 then contacts the fabric filter portion 54 of the sample probe tip filter 50 where the travelling gas stream 18 is captured by the suction force from the analyzer 22 and is sent to the analyzer 22 for analysis. Due to the flow entrainment force and gravimetric force, most of the fly ash particulates (i.e., the relatively medium and large size fly ash particles) follow the flue gas stream 14 within a furnace. The remaining fly ash particulates (i.e., the relatively small particles) entrained within the travelling gas stream 18 (now in flow reversal 66) are captured on the fabric filter 54 (e.g., ten micron size openings) located within the inner concentric pipe 56.

Further, the end 68 of the sample probe tip filter 50 opposite the end that attaches to the analyzer 22 may be fully closed, partially open or fully open, depending on proximity of the sample probe tip filter 50 to any sootblowers, and any direct contact of air (e.g., from sootblowers) at the end 68 of the sample probe tip filter 50. Also, in embodiments the pipe openings 60 may begin at approximately six to ten inches (or any other suitable distance greater than or less than six to ten inches) past the end of the support sleeve pipe 64. Also, in embodiments the opening 62 may begin substantially right after the end of the support sleeve pipe 64 to allow the analyzer exhaust gases 42 to be discharged into the travelling gas stream 18. The opening 62 helps to avoid any analyzer exhaust sample gas from the support sleeve pipe 64 traveling between the concentric pipes 56, 58 from recirculating back to and into the sample probe tip filter 50 by allowing the recirculated gas to exit the sample probe tip filter 50 from the opening 62. The analyzer exhaust sample gas may undesirably affect the accuracy of the sampling of the flue gas if the exhaust sample gas were to recirculate back into the analyzer 22, and the distance from the beginning of the opening 62 from the end of the support sleeve pipe 64 may be chosen as needed to avoid any such undesirable recirculation.

The purposes of the shield 52 are to: 1) deflect (and, thus, reduce) a substantial amount of the fly ash particulates from directly entering into and accumulating onto the sample probe tip filter 50 (e.g., so that primarily the hot travelling gas stream 18 enters the sample probe tip filter 50 and ultimately the analyzer 22 for sampling thereby); and 2) prevent the high velocity travelling gas stream 18 from directly contacting the sample probe tip filter 50, which could damage the fabric tip portion 54 of the filter 50 over time. Typically the shield 52 will deflect the relatively larger fly ash particles from entering the sample probe tip filter 50 and only allow the relatively smaller fly ash particulates along with the travelling gas stream 18 to enter the sample probe tip filter 50.

Figure 3A:
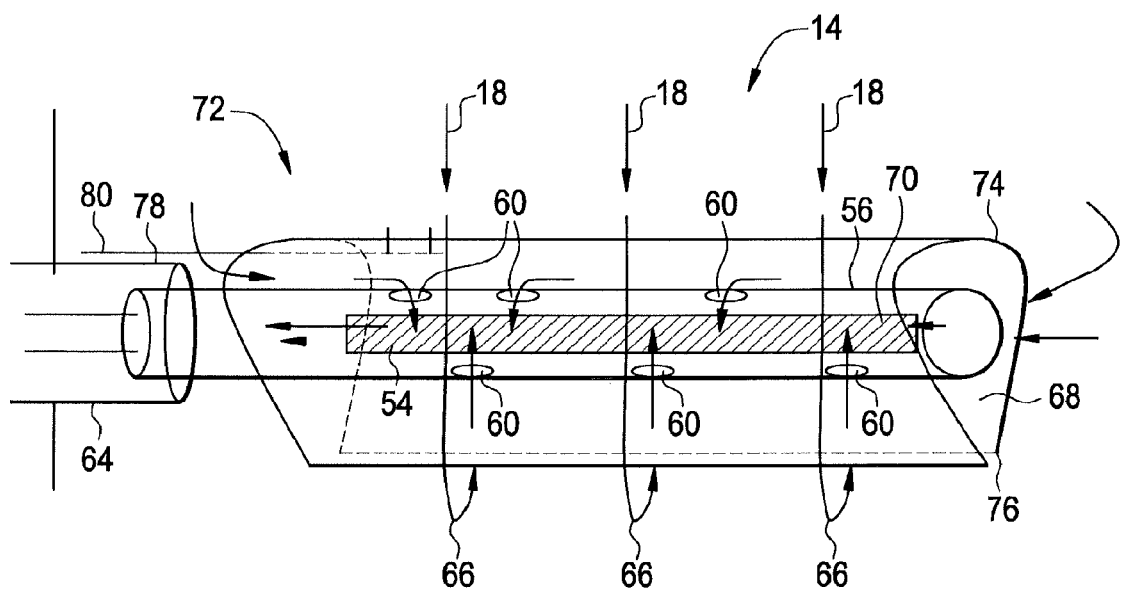
FIGS. 3A and 3B, are side and end views, respectively, that together illustrate a sample probe with a shield in accordance with another embodiment of the invention.
Figure 3B:
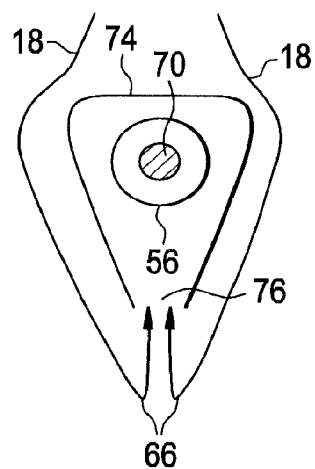

In FIG. 3, including FIGS. 3A and 3B taken together, another embodiment of a sample probe tip filter 70 is provided with a shield configuration 72, which reduces the amount of fly ash particulates within the travelling gas stream 18 that impinge on the probe tip filter 70. The shield 72 of this embodiment is somewhat similar to that of the previous embodiment of FIG. 2 in that the shield 72 also uses a flow reversal technique to reduce the amount of fly ash particulates in the travelling gas stream 18 that enter the sample probe tip filter 70. As such, like reference numbers refer to like elements in FIGS. 2 and 3. In an embodiment, the fabric filter 54 is enclosed within the inner concentric pipe 56. The concentric pipe 56 may have one or more openings 60, similar to the openings in the embodiment of FIG. 2, along its length for the reverse flow sampling flue gas 66 to enter and contact the fabric filter portion 54.

In an embodiment, an outer protective shield 74 is provided that may comprise, for example, an inverted "U"-shaped design with an opening 76 along the bottom of the shield 74, as shown in FIG. 3B. However, the outer protective shield 74 may take on any other suitable design. The outer protective shield 74 connects to the support sleeve pipe 64 by any suitable mechanism (e.g., a pivot 78 attached to the support sleeve pipe 64 and a rod 80 attached both to the pivot 78 and to the outer protective shield 74) such that the outer shield 74 may rotate with the flow of the travelling gas stream 18 or gravity (e.g., for primarily vertical flue gas flow). Through this rotational feature, the opening 76 on the bottom of the outer shield 74 is aligned downstream of the travelling gas stream 18, regardless of the direction of the travelling gas stream 18. In this embodiment (as in the prior embodiment), the use of the flow entrainment force and gravimetric force is made to reduce the amount of fly ash particulates that enter the sample probe tip filter 70. In the embodiment in FIG. 3, the travelling gas stream 18 flows downward within a furnace, and encounters the outer protective shield 74, which diverts the flow of the travelling gas stream 18 around the outer shield 74. The flue gas then makes a 180 degree "U-turn", or directional flow reversal, as illustrated by the lines with arrowheads 66, and flows back through the openings 76, 60 in the outer protective shield 74 and the inner concentric pipe 56, respectively. The flue gas 66 then contacts the fabric filter portion 54 of the sample probe tip filter 70 where the flue gas is captured and sent to the analyzer 22 for analysis. Due to the flow entrainment force and gravimetric force, most of the fly ash particulates (i.e., the relatively large and medium size particles) continue downward within the furnace 14. The remaining fly ash particulates (i.e., the relatively small particles) entrained within the travelling gas stream 18 (now in flow reversal 66) are captured on the fabric filter 54 (e.g., ten micron size openings) located within the inner concentric pipe 56. As with the embodiment of FIG. 2, in the embodiment of FIG. 3 the shield 72 is disposed upstream of the sample probe tip filter 70 in the travelling gas stream 18. Further, the flow of the travelling gas stream 18 need not be directly downward as illustrated in FIG. 3 for embodiments of the shield 72 to operate properly. It is the configuration of the shield 72 combined with the suction force from the analyzer 22 that creates the flow reversal, which then allows only the relatively smaller fly ash particles to enter the sample probe tip filter 57. As noted, the outer protective shield 74 rotates by way of, e.g., the pivot 78 and the rod 80, such that the shield 74 is aligned with the direction of the opening 76 on the bottom of the shield 74 (and, thus, with the direction of the travelling gas stream 18), regardless of the direction of the travelling gas stream 18. Other suitable mechanisms may be used to allow for the rotation of the outer protective shield 74.

Further, the end 68 of the sample probe tip filter 70 opposite the end that attaches to the analyzer 22 may be fully closed, partially open or fully open, depending on proximity of the sample probe tip filter 70 to any sootblowers, and any direct contact of air (e.g., from sootblowers) at the end 68 of the sample probe tip filter 50. Also, in embodiments the openings 60, 76 may begin at approximately six to ten inches (or any other suitable distance greater than or less than six to ten inches) past the end of the support sleeve pipe 64. The opening 76 also helps to avoid any analyzer exhaust sample gas from the support sleeve pipe 64 and the shield 74 from recirculating back to and into the sample probe tip filter 70 by allowing the recirculated gas to exit the sample probe tip filter 70 from the opening 76. The analyzer exhaust sample gas may undesirably affect the accuracy of the sampling of the flue gas if the exhaust sample gas were to recirculate back into the analyzer 22, and the distance from the beginning of the openings 60, 76 from the end of the support sleeve pipe 64 may be chosen as needed to avoid any such undesirable recirculation.

The purposes of the shield 72 are similar to those of the shield 52 of the embodiment of FIG. 2; that is, to: 1) deflect (and, thus, reduce) a substantial amount of the fly ash particulates from directly entering into and accumulating onto the sample probe tip filter 70 (e.g., so that primarily the hot travelling gas stream 18 enters the sample probe tip filter 70 and ultimately the analyzer 22 for sampling thereby); and 2) prevent high velocity flue gas from directly contacting the sample probe tip filter 70, which could damage the filter 70 over time. Typically the shield 72 will deflect the relatively larger fly ash particles from entering the sample probe tip filter 70 and only allow the relatively smaller fly ash particulates along with the travelling gas stream 18 to enter the sample probe tip filter 70.

Embodiments of the invention reduce the amount of hot temperature fly ash from entering into the sampling flue gas analyzer system. This allows for in-situ separation of fly ash from sample flue gas streams in hot temperature furnaces with little or no maintenance required. Embodiments of the present invention may be used to continuously sample flue gas in a hot furnace that carries high loads of fly ash or dust particulates, such as coal fired boiler units, cement kilns or other plants with relatively high particulate loads in their furnace.

Embodiments of the invention comprise filtering concepts that meet the following criteria: 1) reduce the amount of fly ash particulates that enter into the flue gas analyzer sampling system by segregating a substantial amount of the fly ash particulates from the gas sampling stream; 2) protect the sample probe tip filter from any damage that may be caused by high velocity of flue gases, proximity of soot blowers or other damaging devices, by diverting the hot flue gases away from direct contact with the sample probe filter tip; and 3) applies to hot temperature gases in the range of about 900° F. to about 1500° F. This allows embodiments of the invention to perform in-situ hot flue gas sampling in hot combustion furnaces or boilers with relatively high loads of particulates such as fly ash, thereby allowing the flue gas analyzer to be used in a broader range of environmentally harsh dust conditions.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A sample probe, comprising:
   a sample probe tip filter; and
   a shield disposed in relation to the sample probe tip filter, the shield being operable to deflect particles in a gas sampling stream away from the sample probe tip filter, the shield having at least one opening that allows the gas within the gas sampling stream and certain ones of particles in the gas sampling stream both traveling in a substantially flow reversal direction to a primary direction of the gas sampling stream to enter the shield and contact the sample probe tip filter.

2. The sample probe of claim 1, the shield substantially covering the sample probe tip filter.

3. The sample probe of claim 1, the shield comprising at least one pipe that encloses at least a portion of the sample probe tip filter.

4. The sample probe of claim 3, the at least one pipe having at least one opening formed therein to prevent the gas from traveling along the shield to the sample probe tip filter.

5. The sample probe of claim 1, the shield comprising at least two concentric pipes, an inner pipe with the at least two concentric pipes enclosing at least a portion of the sample probe tip filter.

6. The sample probe of claim 5, the inner pipe having at least one opening formed therein to prevent the gas from traveling along the shield to the sample probe tip filter.

7. The sample probe of claim 1, further comprising a support sleeve pipe, wherein the shield is connected directly or indirectly to the support sleeve pipe.

8. The sample probe of claim 1, further comprising a support sleeve pipe, wherein the shield is connected to the support sleeve pipe to allow rotation of the shield with respect to the support sleeve pipe.

9. The sample probe of claim 1, further comprising a support sleeve pipe, wherein rotation of the shield with respect to the support sleeve pipe being in a direction that substantially aligns the at least one opening in the shield with both the gas within the gas sampling stream and the certain ones of the particles in the gas sampling stream traveling in the substantially flow reversal direction with respect to the primary direction of the gas sampling stream.

10. The sample probe of claim 1, the at least one opening in the shield substantially covering a fabric tip portion of the sample probe tip filter.

11. The sample probe of claim 1, a portion of the shield being located upstream of the sample probe tip filter when the sample probe is placed in the gas sampling stream.

12. A sample probe for sampling flue gas in a gas sampling stream, comprising:
a sample probe filter having a tip portion located at one end of the sample probe filter, the tip portion of the sample probe filter being operable to sample the flue gas in the gas sampling stream; and
a shield disposed in relation to the sample probe filter, the shield having a length that at least substantially covers the sample probe filter, the shield being operable to deflect particles in the gas sampling stream away from the sample probe tip filter, the shield having at least one opening that allows the gas within the gas sampling stream and certain ones of particles in the gas sampling stream both traveling in a substantially flow reversal direction to a primary direction of the gas sampling stream to enter the shield through the at least one opening and contact the sample probe tip filter.

13. The sample probe of claim 12, a portion of the shield being located upstream of the sample probe filter when the sample probe is placed in the gas sampling stream.

14. The sample probe of claim 12, the shield comprising at least one pipe that encloses at least a portion of the sample probe tip filter, the at least one pipe having at least one opening formed therein to prevent the gas from traveling along the shield to the sample probe tip filter.

15. The sample probe of claim 12, the shield comprising at least two concentric pipes, an inner pipe with the at least two concentric pipes enclosing at least a portion of the sample probe tip filter.

16. The sample probe of claim 12, further comprising a support sleeve pipe, the shield being connected to the support sleeve pipe to allow rotation of the shield with respect to the support sleeve pipe in a direction that substantially aligns the at least one opening in the shield with both the gas within the gas sampling stream and the certain ones of the particles in the gas sampling stream traveling in the substantially flow reversal direction with respect to the primary direction of the gas sampling stream.

17. A sample probe, comprising:
a sample probe tip filter; and
a shield disposed in relation to the sample probe tip filter such that the shield substantially covers the sample probe tip filter, the shield having an inner pipe and an outer pipe, the outer pipe having at least one opening that allows gas within a gas sampling stream and certain ones of particles in the gas sampling stream both traveling in a substantially flow reversal direction to a primary direction of the gas sampling stream to enter the shield and contact the sample probe tip filter.

18. The sample probe of claim 17, the shield being rotatable in a direction that substantially aligns the at least one opening in the outer pipe with both the gas within the gas sampling stream and the certain ones of the particles in the gas sampling stream traveling in the substantially flow reversal direction with respect to the primary direction of the gas sampling stream.

19. The sample probe of claim 17, the inner pipe having at least one opening formed therein to prevent the gas from traveling along the shield to the sample probe tip filter.

* * * * *